(12) United States Patent
Caroli (10) Patent No.: US 10,378,348 B2
(45) Date of Patent: Aug. 13, 2019

(54) METHOD FOR EVALUATING PROPERTIES OF A FLUID MEDIUM

(71) Applicant: TOTAL SA, Courbevoie (FR)

(72) Inventor: Emmanuel Caroli, Pau (FR)

(73) Assignee: TOTAL SA, Courbevoie (FR)

( * ) Notice: Subject to any disclaimer, the term of this patent is extended or adjusted under 35 U.S.C. 154(b) by 143 days.

(21) Appl. No.: 15/026,857

(22) PCT Filed: Oct. 1, 2014

(86) PCT No.: PCT/IB2014/002334
§ 371 (c)(1),
(2) Date: Apr. 1, 2016

(87) PCT Pub. No.: WO2015/052581
PCT Pub. Date: Apr. 16, 2015

(65) Prior Publication Data
US 2016/0237815 A1 Aug. 18, 2016

(30) Foreign Application Priority Data
Oct. 1, 2013 (EP) .................................. 13306355

(51) Int. Cl.
*E21B 49/08* (2006.01)
*G01N 33/28* (2006.01)
*G16C 20/30* (2019.01)
*G01N 33/24* (2006.01)

(52) U.S. Cl.
CPC ......... *E21B 49/08* (2013.01); *G01N 33/2823* (2013.01); *G16C 20/30* (2019.02); *E21B 2049/085* (2013.01); *G01N 33/24* (2013.01)

(58) Field of Classification Search
CPC .. G01N 33/2823; G01N 33/24; G06F 19/704; E21B 49/08; E21B 2049/085
See application file for complete search history.

(56) References Cited

U.S. PATENT DOCUMENTS

| 2003/0182061 | A1  | 9/2003 | Ferworn et al. |
| 2009/0192768 | A1* | 7/2009 | Zuo ............... G01N 33/2823 703/2 |
| 2010/0228485 | A1* | 9/2010 | Betancourt ........... G01V 11/00 702/13 |

OTHER PUBLICATIONS

International Search Report for PCT/IB2014/002334, dated Mar. 24, 2015, 12 pages.

(Continued)

*Primary Examiner* — Kyle R Quigley
(74) *Attorney, Agent, or Firm* — Patterson Thuente Pedersen, P.A.

(57) ABSTRACT

The present invention relates to a method for determination of fluid characteristics in a well, by
 receiving mass ratios and a molecular ratio;
 converting the mass ratios into molecular ratios based on predetermined molecular weights;
 normalizing the converted molecular ratios with the received molecular ratio;
 minimizing a difference between the normalized molecular ratio and an associated member or an associated sum of members;
 computing an estimated molecular weight ($Mw_{6+}$) function of $(k+11-\alpha\Delta M)$; and
 if a stabilization criteria is met, the steps are iterated with the estimated molecular weight as one of the predetermined molecular weights.

8 Claims, 5 Drawing Sheets

(56) References Cited

OTHER PUBLICATIONS

Written Opinion of the International Searching Authority for PCT/IB2014/002334, dated Mar. 24, 2015, 6 pages.

Montel F.: "Phase equilibria needs for petroleum exploration and production industry", Fluid Phase Equilibria, vol. 84, Apr. 1, 1993 (Apr. 1, 1993), pp. 343-367, XP055105419, ISSN: 0378-3812, DOI: 10.1016/0378-3812(93)85132-6.

Dong C. et al: "New downhole fluid analyzer tool for improved reservoir characterization", SPE International, Offshore Europe, Sep. 4-7, 2007, Aberdeen, Scotland, U.K., vol. 108566, Sep. 4, 2007 (Sep. 4, 2007), pp. 1-11, XP002600653, DOI: 10.2118/108566-PA.

Fujisawa G. et al: "Analyzing Reservoir Fluid Composition In-Situ in Real Time: Case Study in a Carbonate Reservoir", SPE International, SPE Annual Technical Conference and Exhibition, Oct. 5-8, 2003, Denver, Colorado, vol. 84092, 2003, pp. 1-9, XP007923051, DOI: 10.2118/84092-MS.

Betancourt S. S. et al: "Exploration Applications of Downhole Measurement of Crude Oil Composition and Fluorescence", SPE International, SPE Asia Pacific Conference on Integrated Modelling for Asset Management, Mar. 29-30, 2004, Kuala Lumpur, Malaysia, vol. 87011, 2004, pp. 1-10, XP007923052, DOI: 10.2118/87011-MS.

\* cited by examiner

METHOD FOR EVALUATING PROPERTIES OF A FLUID MEDIUM

RELATED APPLICATIONS

The present application is a National Phase entry of PCT Application No. PCT/IB2014/002334, filed Oct. 1, 2014, which claims priority from EP Patent Application No. 13306355.2, filed Oct. 1, 2013, said applications being hereby incorporated by reference herein in their entirety.

FIELD OF THE INVENTION

The present invention relates to the domain of fluid characteristics measurements and especially to the domain of the determination of fluid/gas characteristics in a well.

BACKGROUND OF THE INVENTION

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section. Furthermore, all embodiments are not necessarily intended to solve all or even any of the problems brought forward in this section.

During the drilling of a well or during the "open hole" period of the drilled well, it may be advantageous to characterize, in real time, the gas (or more generally the fluid) in the well.

For instance, it may be interesting to determine the proportion of each cut of C1-C30 in the fluid (i.e. molecules that have 1 to 30 carbon atoms).

If it is possible to determine the individual proportion and characteristic of each cut C1-C30 in a given fluid in laboratories, no industrial method/device may be used in a well to determine such proportions and characteristics for each of them.

For instance, mud gas measurements (e.g. "Gas While Drilling" or GWD) have a sufficient level of reliability to consider that the composition of the cuts C1 to C5 (eventually C6) may be determined all along the well. Nevertheless, no individual information regarding the cuts above $C_6$, i.e. $C_{i>6}$ cuts (i.e. molecules with i carbons, i being strictly higher than 6) may be drawn from GWD measurements: such measurements are limited to the light end of the fluid and, consequently, cannot provide straightforward conclusions on the fluid nature and properties.

In addition, "Downhole Fluid Analysis" (or DFA, which is a measurement method based mainly on optical analysis of the fluid at given coordinates in the well) may provide real time measurements of fluid properties while pumping out the reservoir fluid at selected stations (i.e. at selected elevation values). These DFA methods provide information on composition of groups of molecules, for instance, the group of C1, the group of C2-C5 or the group of C6+ (i.e. the molecules with 6 or more than 6 carbons). DFA methods also provide GOR (for "Gas oil ratio") and live downhole fluid density. Nevertheless, no individual information regarding the individual cuts above $C_6$, i.e. $C_{i>6}$ cuts (i.e. molecules with i carbons, i being strictly higher than 6) may be drawn from DFA measurements: DFA only provide the grouped weight concentration of the C6+ group.

In brief, the mud gas service (GWD) cannot quantify full cuts heavier than C6 and optical fluid techniques (DFA) only deliver a lumped C6+ cut at selected stations (i.e. at selected elevation values).

Based on this sparse set of data (C1 to C5 and C1, C2-C5, C6+), there is a need to determine information on higher full cuts (for instance, C7, . . . , C30) in a thermodynamically consistent and vertically continuous approach.

SUMMARY OF THE INVENTION

The invention relates to a method of determination of fluid characteristics in a well. Said method comprises:
/a/ receiving mass ratios, each mass ratio being associated with a set of hydrocarbon cuts, and receiving a molecular ratio, said molecular ratio being associated with a set of hydrocarbon cuts;
/b/ converting received mass ratios into molecular ratios based on predetermined molecular weights, each predetermined molecular weights being associated an element in the sets of hydrocarbon cuts;
/c/ normalizing converted molecular ratios with the received molecular ratio;
/d/ determining parameters $(\alpha,\beta)$ of a sequence defined by $$x_n = \alpha\left(1 - \frac{\beta}{n}\right)x_{n-1},$$

each normalized molecular ratio being associated with a member of the sequence or a sum of members of the sequence, at least a difference between said normalized molecular ratio and the associated member or the associated sum of members being minimized;
/e/ computing an estimated molecular weight function of $$\left(k + \frac{1}{1-\alpha}\right)\Delta M,$$

where k being an integer and $\Delta M$ being a predetermined value representing an molecular weight increment between two hydrocarbon cuts;
/f/ if a stabilization criteria is met, the steps /b/ to /f/ are iterated with the estimated molecular weight as one of the predetermined molecular weights in step /b/;
/g/ outputting the values of the parameters determined in step /d/.

Mass ratios are often provided by DFA measurements. For instance, the mass ratio $x_{m1}$ may be associated with the set of hydrocarbon cuts C1, the mass ratio $x_{m2-5}$ may be associated with the set of hydrocarbon cuts C2-C5, mass ratio $x_{6+}$ may be associated with the set of hydrocarbon cuts C6 and above.

The received molecular ratio is, for instance, a molecular ratio of a cut (e.g. C1 or C3) provided by GWD measurements.

It also is possible to receive additional molecular ratios information in order to increase the resolution of the determination of step /d/. For instance, such molecular ratios may be related to C1 to C5 cuts and provided by GWD measurements. In that case, it is also possible to normalize such additional molecular ratios with the molecular ratio received in step /c/.

Each set of cuts having a molecular weight (e.g. the molecular weight of the set of cuts C2-C5 may be noted Mw$_{2-5}$), it may be possible to multiply the molecular weight (e.g. Mw$_{2-5}$) by the mass ratio (e.g. x$_{m2-5}$) to obtain a molecular ratio (e.g. of cut C2-C5).

The converted/normalized molecular ratio of cut k (respectively k−1) is associated with the member x$_k$ of the sequence (respectively the sum of the members x$_k$ to x$_1$).

Therefore, the parameter (α,β) may be determined and thus, any molecular ratio x$_n$=

$$\alpha\left(1-\frac{\beta}{n}\right)x_{n-1}$$

(n being an integer) may be computed for a given elevation value.

The normalization with an external molecular ratio may ease the convergence of the value of the molecular weight. Without such normalization, the molecular weight may not converge.

In addition, the estimated molecular weight may represent hydrocarbon cuts having more than k carbons.

In a possible embodiment, the stabilization criteria of step /f/ may comprise at least one following condition:
- an absolute difference of a value of α between two iterations of steps /b/-/f/ is lower than a predetermined threshold;
- an absolute difference of a value of the estimated molecular weight between two iterations of steps /b/-/f/ is lower than a predetermined threshold;
- a number of iteration of steps /b/-/f/ exceeds a predetermined value.

For instance, ΔM may be initially set to a value between 12 and 14.

In a possible embodiment, ΔM may be initially set a mean value for various fluids compositions examined in laboratory conditions.

The invention relates also to a broader method to determine fluid characteristics for a plurality of elevation values in a well which enables the above mentioned method. Said latter method may comprise:
- /i/ determining a plurality of values α by executing steps /a/ to /g/ of the above methods for each of the elevation values;
- /ii/ determining a mean molecular weight increment value by computing a plurality of values $$\frac{RT}{g(z_i-z_j)}\ln\left(\frac{\alpha(z_i)}{\alpha(z_j)}\right), z_i$$

being an elevation value in the plurality of elevation values and α(z$_i$) being the determined value α in step /i/ for the elevation value z$_i$, z$_j$ being an elevation value in the plurality of elevation values different from z$_i$ and α(z$_j$) being the determined value α in step /i/ for the elevation value z$_j$;
- /iii/ if a stabilization criteria is met, the steps /i/ to /iii/ are iterated with the mean molecular weight increment value as ΔM in step /e/.
- /iv/ outputting the values of the parameters determined in step /i/ and the mean molecular weight increment value determined in step /ii/.

Then, it is possible to determine, for any elevation value z, any molecular ratio $$x_n = \alpha\left(1-\frac{\beta}{n}\right)x_{n-1}$$

(n being an integer), assuming that $$\alpha(z+dz) = \alpha(z) \cdot e^{\frac{\Delta M_{ij}g(dz)}{RT}}.$$

In addition, the stabilization criteria of step /iii/ may comprise at least one following condition:
- an absolute difference of a value of the mean molecular weight increment value between two iterations of steps /i/-/iii/ is lower than a predetermined threshold;
- a number of iteration of steps /i/-/iii/ exceeds a predetermined value.

A second aspect relates to a computer program product comprising a computer readable medium, having thereon a computer program comprising program instructions. The computer program is loadable into a data-processing unit and adapted to cause the data-processing unit to carry out the method described above when the computer program is run by the data-processing unit.

Other features and advantages of the method and apparatus disclosed herein will become apparent from the following description of non-limiting embodiments, with reference to the appended drawings.

BRIEF DESCRIPTION OF THE DRAWINGS

The present invention is illustrated by way of example, and not by way of limitation, in the figures of the accompanying drawings, in which like reference numerals refer to similar elements and in which.

DESCRIPTION OF PREFERRED EMBODIMENTS

Figure 1:
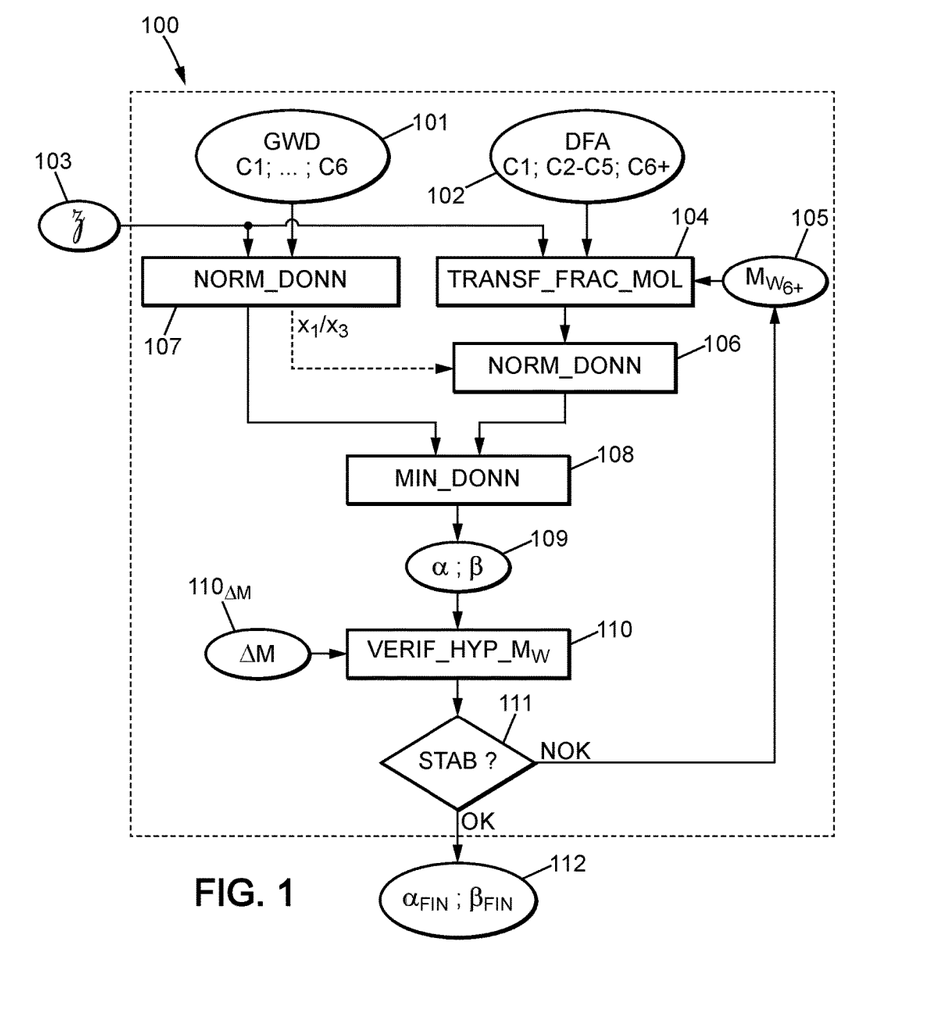
FIG. 1 is a flow chart describing a possible embodiment of the present invention to determine any molecular fraction for a given elevation value.

FIG. 1 is a flow chart describing a possible embodiment of the present invention to determine any molecular fraction for a given elevation value.

In order to describe the relation between concentrations of various cuts, it is possible to develop models. These models should be able to provide a simplified but robust fluid description theory adapted to the mudlogging and sampling contexts and based on few measurements, possibly biased (OBM filtrate pollution, mud gas contaminants . . . ).

For instance, it is possible to use a model developed by Montel F. (1993) which postulates that the molecular fraction x$_n$ of the hydrocarbon cut of rank n is related to the previous cut concentration x$_{n-1}$ by the formula:

$$x_n = \alpha\left(1 - \frac{\beta}{n}\right)x_{n-1}$$

with α, β two parameters to be determined.

The two α and β parameters (both comprised between 0 and 1, unitless) characterize the chemistry of a hydrocarbon fluid at a given depth; α mainly controls the concentration of heavy cuts while β drives the light ones. α deals with the logarithmic decay of the concentration of each cut while β adds an extra-curvature to the composition pattern.

When known, α and β can be used to predict a fluid composition (i.e. $x_n$ for each n in [1;30] for instance) by extrapolating the concentration of a given cut to the next ones.

When unknown, α and β may be determined based on a regression approach (for instance). To determine α and β, the following steps may be executed.

It is possible to receive GWD measurements (101) of various lights cuts (for instance C1 to C6 or to Ck, with k>1) for each elevation values z in the well. These GWD measurements are values representing molecular ratio of the different cuts. These measurements are optional as they improve the resolution of the below process but are not mandatory.

In addition, it is possible to receive DFA measurements (102) of various grouped cuts (for instance C1, C2-C5 and C6+ or Ck+) for various elevation values in a set of values $\{z_1, \ldots, z_n\}$ in the well. These DFA measurements are values representing mass ratio of the different group of cuts.

For DFA values at a given elevation value z (103), it is possible to convert them into molecular ratio (step 104). Indeed, the molecular weight (Mw) of each cut in C1, C2, C3, C4, C5 ($Mw_1$, $Mw_2$, $Mw_3$, $Mw_4$, $Mw_5$) may be known (e.g. tabulated values) and the molecular weight of the grouped cut C6+ ($Mw_{6+}$) may be approximated by a first mean value (105) of different known fluids examined in laboratory conditions.

Once, this transformation performed (i.e. mass ratio value transformed into molecular ratio value), it is possible to normalize the DFA values (step 106). This normalization may comprise the division of each converted cuts values (of cuts C1, C2-C5 and C6+) by a value of any other cut (e.g. C3) expressed originally in molecular fraction (molecular ratio received from GWD measurement for instance). The normalized values of DFA values are noted: $x_{1\text{-}DFA}$, $x_{2\text{-}5\text{-}DFA}$, $x_{6+\text{-}DFA}$.

It is also possible to normalize the GWD values (step 107). This normalization may comprise the division of each received cuts values (of cuts C1, C2, C3, C4, C5 and C6) by the values of the same cut used for the normalization of the DFA converted cuts values. The normalized values of GWD values are noted: $x_{1\text{-}CWD}$, $x_{2\text{-}CWD}$, $x_{3\text{-}GWD}$, $x_{4\text{-}GWD}$, $x_{5\text{-}GWD}$, $x_{6\text{-}CWD}$.

The normalizations make possible the comparison of GWD and DFA measurements and increase the convergence.

Once, DFA values and GWD values are normalized, the values α and β (109) are determined (step 108). For instance, this determination is based on the minimization of the sum (or weighted sum) of distances (i.e. the distance between x and y being d(x,y)) of the values of the curve defined by $$x_n = \alpha\left(1 - \frac{\beta}{n}\right)x_{n-1}$$

and the normalized values of DFA and/or GWD. For instance, the distances to minimize may be:

$d(x_1, x_{1\text{-}GWD})$ and $d(x_1, x_{1\text{-}DFA})$;
$d(x_2, x_{2\text{-}GWD})$;
$d(x_3, x_{3\text{-}GWD})$;
$d(x_4, x_{4\text{-}GWD})$;
$d(x_5, x_{5\text{-}GWD})$;
$d(\Sigma_{i=2}^{5} x_i, x_{2\text{-}5\text{-}DFA})$;
$d(x_6, x_{6\text{-}GWD})$;
$d(\Sigma_{i=6}^{\infty} x_i, x_{6+\text{-}DFA})$.

In addition, it is possible to include in the minimization process some additional distances based on ratio. For instance:

$$-d\left(\frac{\sum_{i=3}^{5} x_i}{\sum_{i=3}^{\infty} x_i}, \frac{x_{3\text{-}5\text{-}DFA}}{x_{3\text{-}6+\text{-}DFA}}\right).$$

In a possible embodiment, it is possible to exclude from the minimization process the distance with cuts C1 and C2 alone (e.g. $d(x_1, x_{1\text{-}GWD})$, $d(x_1, x_{1\text{-}DFA})$, and $d(x_2, x_{2\text{-}GWD})$) as these distances may carry artefacts/noises related to biological phenomena.

As α and β are values in [0;1], it is possible to start the minimization process (of a sum of above mentioned distances) with α=0.5 and β=0.5 and modify α and β (for instance, by dichotomy) to improve the computed sum. For instance, it is possible to compute every possible couple (α; β) in $[0;1]^2$ with a step of 0.001 (for instance) and to determine (α; β) that minimizes the computed sum.

The minimization process may compute the sum of the square of each above mentioned distances instead of simply the sum of said distances (mean-square method).

Once, α and β are determined (109), the value of $Mw_{6+}$ is computed (step 110) based on the following formula:

$$Mw(Ck+) = Mw_{k+} = \left(k + \frac{1}{1-\alpha}\right)\Delta M$$

with ΔM(g/mol) is the molecular weight increment between two subsequent cuts, generally comprised for pure alkanes between 12 (one carbon increment) and 14 g/mol (a —CH2- increment) and k a cut value (for instance set to 6 for computing $Mw_{6+}$).

The value of ΔM ($110_{\Delta M}$) is first set to an arbitrary value between 12 and 14 (for instance 13 or a mean value for various fluids compositions examined in laboratory conditions).

The test 111 verifies a stabilization criterion. Such stabilization criterion may comprise one below condition or a combination (and/or) of below conditions:

the value of α is stabilized (i.e. the absolute difference between the value of α before the execution of steps 104 to 110 and after the execution of steps 104 to 110 is lower than a certain threshold, for instance $10^{-6}$). If the value of α is not yet set/determined before the execution of steps 104 to 110, α may be set to a predetermined and arbitrary value (e.g. 1 or 0).

the value of $Mw_{6+}$ is stabilized (i.e. the absolute difference between the value of $Mw_{6+}$ before the execution of steps 104 to 110 and after the execution of steps 104 to 110 is lower than a certain threshold, for instance $10^{-6}$).

the number of reiteration of steps 104, 106, 108, 109, 110 and 111 exceeds a predetermined number (e.g. 1000 iterations).

If the stabilization criterion is not verified (i.e. all conditions or at least one condition is not met, test 111, output NOK), the steps 104, 106, 108, 109, 110 and 111 are reiterated.

If the stabilization criterion is verified (i.e. all conditions or at least one condition is met, test 111, output OK), the values of $\alpha$ and $\beta$ are output (112).

Thanks to the determination of $\alpha$ and $\beta$ for the elevation value z, it is then possible to determine any molecular fraction $x_n$ of the hydrocarbon cut of rank n (at the elevation value z) by applying the following formula $$x_n = \alpha\left(1 - \frac{\beta}{n}\right)x_{n-1}$$

and by knowing at least $x_1$.

Figure 2:
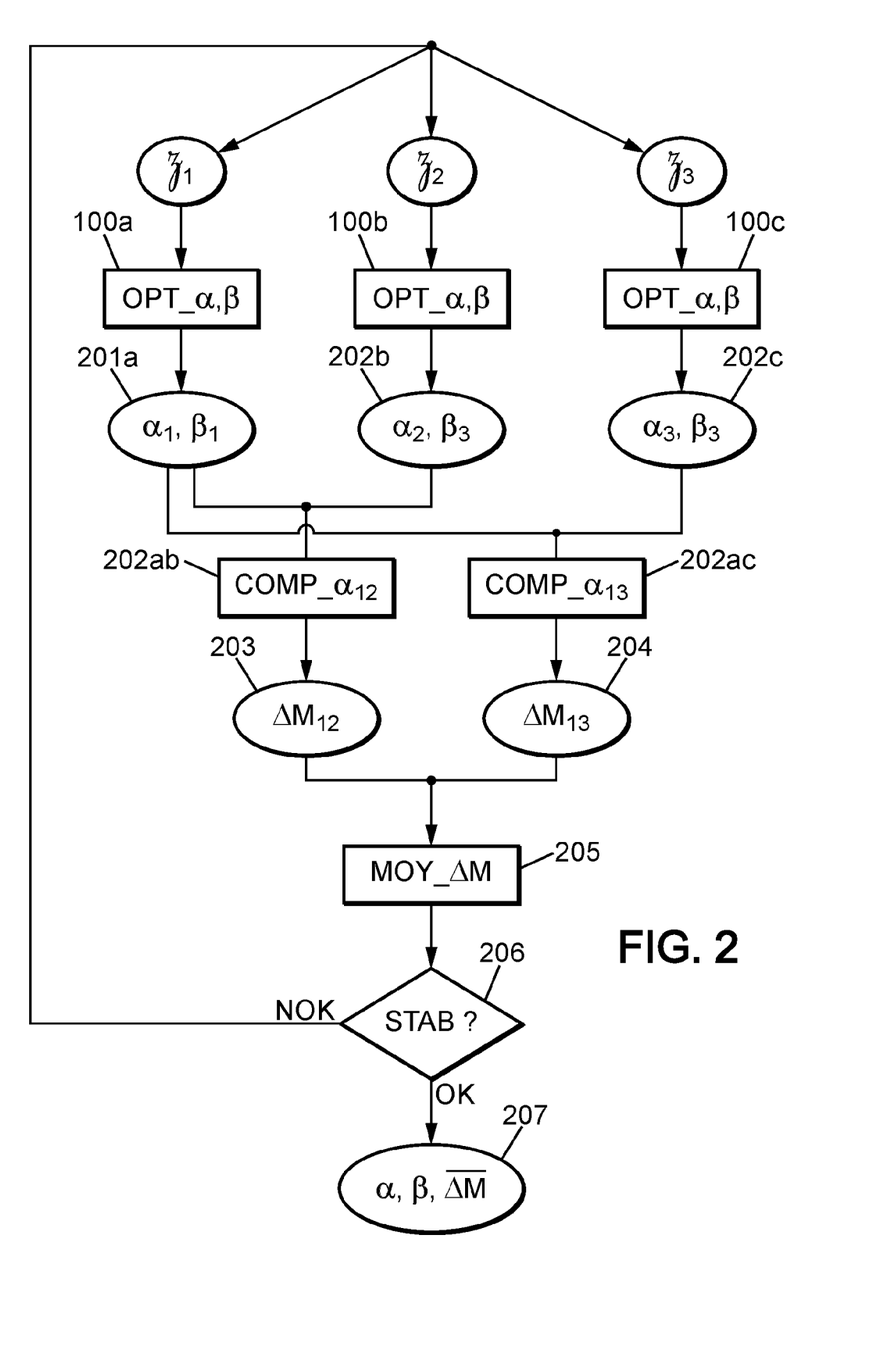
FIG. 2 is a flow chart describing a possible embodiment of the present invention to determine any molecular fraction for any elevation values.

FIG. 2 is a flow chart describing a possible embodiment of the present invention to determine any molecular fraction of cuts for any elevation values.

In this embodiment, the process described in FIG. 1 (i.e. the block 100) is executed for a plurality of elevation values $z_1$, $z_2$, $z_3$, etc. (i.e. step 100a for $z_1$, step 100b for $z_2$, step 100c for $z_3$, etc.). The plurality of elevation values are elevation values of DFA measurements.

Therefore, a plurality of couples $\alpha$ and $\beta$ (i.e. 201a, 202b, 202c, etc.) may be determined as the output of the processes 100a, 100b, 100c, etc. Once these plurality of couples ($\alpha$; $\beta$) are determined, it is possible to determine (steps 202ab, 202ac, etc.), for each couple $(z_i; z_j)_{i>j}$, a molecular weight increment $\Delta M_{ij}$ based on the following formula:

$$\alpha(z_i) = \alpha(z_j) \cdot e^{\frac{\Delta M_{ij} g(z_i - z_j)}{RT}}$$

with g the gravitational constant, T the mean temperature at elevation values $z_i$ and $z_j$, R the gas constant.

$$\Delta M_{ij} = \frac{RT}{g(z_i - z_j)} \ln\left(\frac{\alpha(z_i)}{\alpha(z_j)}\right)$$

Therefore, if the process 100 is executed for n elevation level $$C_n^2 = n \cdot \frac{n-1}{2}$$

molecular weight increments $\Delta M_{ij}$ are determined (e.g. 203, 204).

Thus, it is possible to determine $\overline{\Delta M}$, the mean value of all determined molecular weight increments $\Delta M_{ij}$ (step 205).

If the value $\overline{\Delta M}$ is stabilized (i.e. the value of $\overline{\Delta M}$ is very close to the value of the molecular weight increment $\Delta M$ used in step 110 of FIG. 1, e.g. the difference being less than $10^{-6}$ g/mol) (test 206, output OK), the values of ($\alpha$; $\beta$) for each elevation level and the value of $\overline{\Delta M}$ are returned (207).

If the value $\overline{\Delta M}$ is not stabilized, the value of $\Delta M$ used in step 110 of FIG. 1 is replaced by the value of $\overline{\Delta M}$ and the steps 100a, 100b, 100c, 201a, 201b, 201c, 202ab, 202ac, 203, 204, 205, 206 are reiterated.

Test 206 may also take into account a maximal number of iterations (e.g. if the number of iteration is greater than a predetermined number of times, the values of ($\alpha$; $\beta$) for each elevation value and the value of $\overline{\Delta M}$ are returned (207)).

Thanks to the determination of $\alpha$, $\beta$ and $\overline{\Delta M}$ for a plurality of elevation values, it is then possible to determine any molecular fraction $x_n$ of the hydrocarbon cut of rank n (at any elevation value z) by applying the following formulas $$x_n = \alpha\left(1 - \frac{\beta}{n}\right)x_{n-1} \text{ and } \alpha(z + dz) = \alpha(z) \cdot e^{-\frac{\Delta M_{ij} g(dz)}{RT}}$$

(by knowing at least $x_1$ for each elevation value z).

$$Mw_{k+} = \left(k + \frac{1}{1-\alpha}\right)\overline{\Delta M}$$

may also be determined based on the knowledge of $\alpha$ and $\overline{\Delta M}$ (at any elevation value z)

Figure 3:
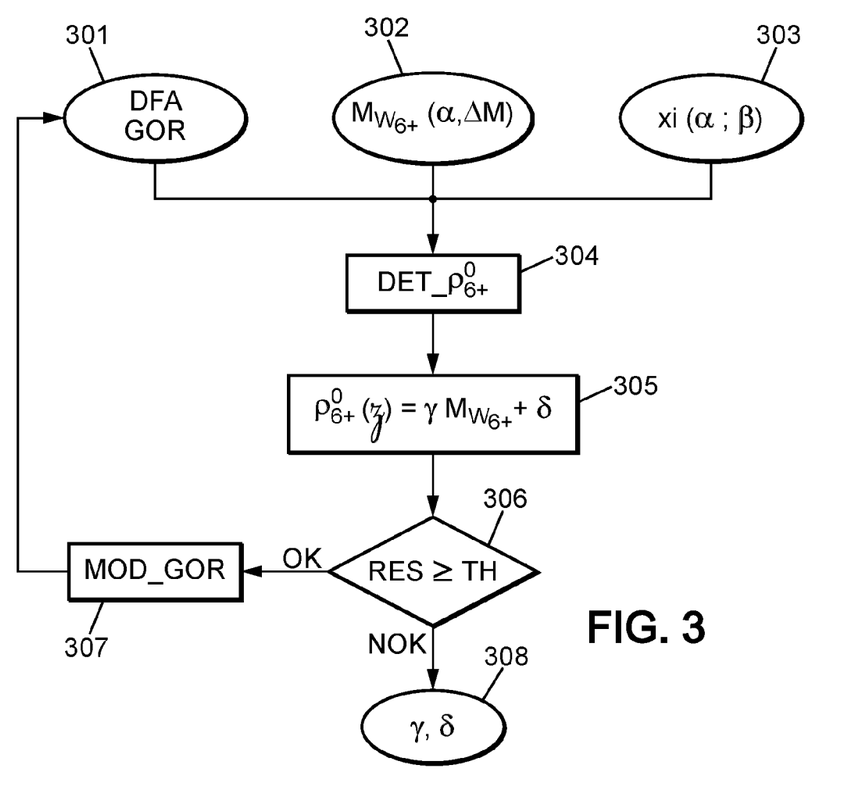
FIG. 3 is a flow chart describing a possible determination of the molecular volume for a group of cuts C6+.

FIG. 3 is a flow chart describing a possible determination of the molecular volume for any elevation value and for a group of cuts C6+.

The molecular volume for full cuts C1 to C5 may be known and tabulated. Nevertheless, the molecular volume for the group of cuts C6+ is unknown due to the presence of isomers in the various cuts above C6.

To determine the molecular volume for the group of cuts C6+ (i.e. $\rho_{6+}^0(z)$), the gas-oil volume ratio at the surface (or GOR, 301) obtained by DFA measurements is received.

In addition, the molecular weight of the group of cuts C6+ (302) may be obtained based on the above mentioned formula $$Mw(C6+) = Mw_{6+} = \left(6 + \frac{1}{1-\alpha}\right)\Delta M,$$

$\alpha$ being determined thanks to the process described in relation to FIG. 1 and $\Delta M$ being determined thanks to the process described in relation to FIG. 2.

Furthermore, it is possible to determine the molecular ratio $x_i$ (303) of each cuts i (i>0, i integer) thanks to the values of $\alpha$ and $\beta$ determined by the process described in relation to FIG. 1:

$$x_n = \alpha\left(1 - \frac{\beta}{n}\right)x_{n-1},$$

the first values of $x_i$ being known thanks to the GWD measurements.

Thus, once all these values received, it is possible to determine the molecular volume for the group of cuts C6+ (step 304) for each elevation values where a DFA measurement is performed. Indeed, it is possible to express that:

$$\rho_{k+}^0(z) = \frac{x_{k+}^L M w_{6+} GOR \cdot \rho_G^0}{\left(\sum_{i=p}^{k} x_i^L \cdot M w_i\right) \left(\frac{\sum_{i=1}^{p-1} x_i \cdot M w_i}{\sum_{i=p}^{k} x_i \cdot M w_i}\right) - GOR \cdot \rho_G^0 \sum_{i=p}^{k-1} \frac{x_i^L \cdot M w_i}{\rho_i^0}}$$

(k = 6, for instance)

considering that:
- p is an integer representing the rank of the first cut in the liquid phase, it is assumed that C1 to Cp−1 are gas fluid and that cuts above Cp are liquid fluid (e.g. p equals, most of the time, 4 or 5);
- $\rho_G^0$ being the molecular density of the gas at the surface level of the well extracted from the oil (this value is known as the value are tabulated as p<6);
- $x_i^L$ being the molecular ratio of the cut Ci in the liquid cuts $$x_j^L = \frac{x_j}{\sum_{i=p}^{q} x_i};$$

Indeed, the GOR value may be expressed by the following formula:

$$GOR = \frac{\sum_{i=1}^{p-1} \frac{x_i \cdot M w_i}{\rho_G^0}}{\sum_{i=p}^{q} \frac{x_i \cdot M w_i}{\rho_L^0}}$$

$\rho_L^0$ being the molecular density of the liquid at the surface level of the well $\rho_L^0 =$ $$\frac{\sum_{i=p}^{q} x_i^L \cdot M w_i}{\sum_{i=p}^{q} \frac{x_i^L \cdot M w_i}{\rho_i^0}};$$

q is an integer representing the rank of the last cut in the liquid phase (e.g. q=30 or 60, etc.);

Once the molecular volume for the group of cuts C6+ (step 304) $\rho_{6+}^0(z)$ are determined for a plurality of elevation values z (these elevation values are elevation values of stations where DFA measurements took place), it is verified that the values $\rho_{6+}^0(z)$ are proportional to the values of Mw$_{6+}$(z). In particular, the coefficients γ and δ are determined (step 305) to minimize the distance of points of coordinates ($\rho_{6+}^0(z)$, Mw$_{6+}$(z)) (z in the elevation values stations where DFA measurements took place) with the curve defined by γ. Mw$_{6+}$(z)+δ.

If the residue of the minimization (e.g. the sum of the distances of points of coordinates ($\rho_{6+}^0(z)$, Mw$_{6+}$(z)) with the defined curve γ. Mw$_{6+}$(z)+δ) is bigger than a predetermined threshold (test 306, output OK), the measured GOR value is modified within the known uncertainty range defined per tool type (because it is assumed that the GOR value may comprise important level of noises during the measurements) (step 307). This modification of the GOR value (which is in the interval [0,1]) may be performed by dichotomy.

If the residue of the minimization is not bigger than a predetermined threshold (test 306, output NOK), the value of γ and δ are returned (308).

Test 306 may also take into account a maximal number of iterations (e.g. if the number of iteration is greater than a predetermined number of times, the values of γ and δ are returned, 308).

Then, based on the values of γ, δ, and Mw$_{6+}$(z), it is possible to determine any molecular volume for any elevation value and for a group of cuts C6+ by applying the following formulae:

$$\rho_{6+}^0(z) = \gamma \cdot M w_{6+}(z) + \delta$$

$$\rho_0(z) = \frac{\sum_{i=1}^{q} x_i \cdot M w_i}{\sum_{i=1}^{q} \frac{x_i \cdot M w_i}{\rho_i^0}}$$

Figure 4:
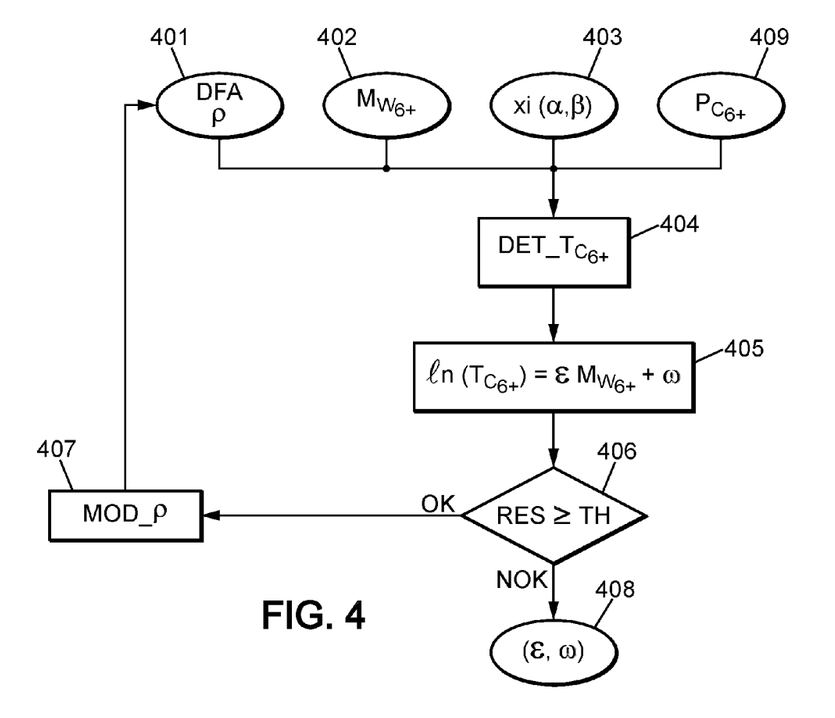
FIG. 4 is a flow chart describing a possible determination of the critical temperature for a group of cuts C6+.

FIG. 4 is a flow chart describing a possible determination of the critical temperature for a group of cuts C6+.

To determine the critical temperature for the group of cuts C6+ (i.e. Tc$_{6+}$(z)), the downhole fluid density (derived from pressure gradients and/or downhole measurements like DFA, or ρ(z) 401) is received.

In addition, the molecular weight of the group of cuts C6+ (402) may be obtained based on the above mentioned formula $$Mw(C6+) = Mw_{6+} = \left(6 + \frac{1}{1-\alpha}\right)\Delta M,$$

α being determined thanks to the process described in relation to FIG. 1 and ΔM being determined thanks to the process described in relation to FIG. 2.

Furthermore, it is possible to determine the molecular ratio $x_i$ (403) of each cuts i (i>0, i integer) thanks to the values of α and β determined by the process described in relation to FIG. 1

$$x_n = \alpha\left(1 - \frac{\beta}{n}\right)x_{n-1},$$

the first values of $x_i$ being known thanks to the GWD measurements.

The critical pressure of the group of cuts C6+ may be determined by tabulated data as this value is quite well regular and predictable. Therefore it is possible to use a predetermined function or abacus (409) to determine the critical pressure of the group of cuts C6+ (i.e. Pc$_{6+}$, function of the molecular weight, for instance)

Thus, once all these values are received, it is possible to determine Tc$_{6+}$, the critical temperature for the group of cuts C6+ (step 404) for each elevation values where a DFA measurement is performed. Indeed, it is possible to express that:

$$\rho(z) = \rho(P, T) = \rho_0 \cdot \frac{C(P_0, T_0)}{C(P, T)}$$

considering that:
C(P,T) is a surface-to-downhole correction function, $C(P,T) = \sum_{k=0}^{3} (\sum_{j=0}^{4} A_{kj} \cdot Prj \cdot Trk)$,
$A_{kj}$ are predetermined constants;
(Pr,Tr) are, respectively, the reduced pressure (=P/Pc) and temperature (=T/Tc);
$P_0$ and $T_0$ are the standard conditions (respectively, 1 atm and 15° C.);

$$\rho_0 = \frac{\sum_{i=1}^{q} x_i \cdot Mw_i}{\sum_{i=1}^{q} \frac{x_i \cdot Mw_i}{\rho_i^0}};$$

q is an integer representing the rank of the last cut in the liquid phase (e.g. q=30 or 60, etc.);
$Tc_1$ to $Tc_5$ are known and tabulated values.
Therefore, it is possible to write that:

$$\rho(z) = \frac{\sum_{i=1}^{q} x_i \cdot Mw_i}{\sum_{i=1}^{q} \frac{x_i \cdot Mw_i}{\rho_i^0}} \cdot \frac{\sum_{k=0}^{3} \left(\sum_{j=0}^{4} A_{kj} \cdot \left(\frac{P_o}{Pc}\right)^j\right) \cdot \left(\frac{T_o}{Tc}\right)^k}{\sum_{k=0}^{3} \left(\sum_{j=0}^{4} A_{kj} \cdot \left(\frac{P}{Pc}\right)^j\right) \cdot \left(\frac{T}{Tc}\right)^k}$$

In addition, it is noted that $Tc = \sum_{i=1}^{\infty} x_i Tc_i = (\sum_{i=1}^{5} x_i Tc_i) + x_{6+} Tc_{6+}$ and $Pc = \sum_{i=1}^{\infty} x_i Pc_i = (\sum_{i=1}^{5} x_i Pc_i) + x_{6+} Pc_{6+}$. Each $x_i$ may be known according to the method described in relation to FIG. 1. Each $Tc_i$ and $Pc_i$ (for i<6) are known and tabulated. As detailed above, the critical pressure of the group of cuts C6+ (i.e. $Pc_{6+}$) may be determined thanks to an abacus. Therefore, only $Tc_{6+}$ is unknown.

$$\rho(z) = \frac{\sum_{i=1}^{q} x_i \cdot Mw_i}{\sum_{i=1}^{q} \frac{x_i \cdot Mw_i}{\rho_i^0}} \cdot \frac{\sum_{k=0}^{3} \left(\sum_{j=0}^{4} A_{kj} \cdot \left(\frac{P_o}{\left(\sum_{i=1}^{5} x_i Pc_i\right) + x_{6+} Pc_{6+}}\right)^j\right) \cdot \left(\frac{T_o}{\left(\sum_{i=1}^{5} x_i Tc_i\right) + x_{6+} Tc_{6+}}\right)^k}{\sum_{k=0}^{3} \left(\sum_{j=0}^{4} A_{kj} \cdot \left(\frac{P}{\left(\sum_{i=1}^{5} x_i Pc_i\right) + x_{6+} Pc_{6+}}\right)^j\right) \cdot \left(\frac{T}{\left(\sum_{i=1}^{5} x_i Tc_i\right) + x_{6+} Tc_{6+}}\right)^k}$$

Once $Tc_{6+}$ is determined (step 404, resolution of the above formula that contains only one unknown value, for instance by non-analytical method) for a plurality of elevation values z (these elevation values are elevation values of stations where DFA measurements took place), it is verified that the values $\ln(Tc_{6+}(z))$ are proportional to the values of $Mw_{6+}(z)$.

In particular, the coefficients $\in$ and $\omega$ are determined (step 405) to minimize the distance of points of coordinates ($\ln(Tc_{6+}(z))$, $Mw_{6+}(z)$) (z in the elevation values stations where DFA measurements took place) with the curve defined by $\in \cdot Mw_{6+}(z) + \omega$.

If the residue of the minimization (e.g. the sum of the distances of points of coordinates ($\ln(Tc_{6+}(z))$, $Mw_{6+}(z)$) with the defined curve $\in \cdot Mw_{6+}(z) + \omega$) is bigger than a predetermined threshold (test 406, output OK), the measured downhole fluid density value is modified within the known uncertainty range defined per tool type (because it is assumed that the downhole fluid density value may comprise important level of noise during the measurements) (step 407). This modification of the downhole fluid density value may be performed by dichotomy.

If the residue of the minimization is not bigger than a predetermined threshold (test 406, output NOK), the value of $\in$ and $\omega$ are returned (408).

Test 406 may also take into account a maximal number of iterations (e.g. if the number of iteration is greater than a predetermined number of times, the values of $\in$ and $\omega$ are returned, 408).

Then, based on the values of $\varepsilon$, $\omega$, and $Mw_{6+}(z)$, it is possible to determine any compressibility factor C(P,T,z) for any elevation value by applying the following formulae:

$$\ln(Tc_{6+}(z)) = \varepsilon \cdot Mw_{6+}(z) + \omega$$

$$C(P, T, z) = \sum_{k=0}^{3} \left(\sum_{j=0}^{4} A_{kj} \cdot \left(\frac{P(z)}{Pc(z)}\right)^j\right) \cdot \left(\frac{T(z)}{Tc(z)}\right)^k;$$

$$Pc(z) = \left(\sum_{i=1}^{5} x_i(z) \cdot Pc_i\right) + x_{6+}(z) \cdot Pc_{6+}(z)$$

$$Tc(z) = \left(\sum_{i=1}^{5} x_i(z) \cdot Tc_i\right) + x_{6+}(z) \cdot Tc_{6+}(z)$$

Figure 5:
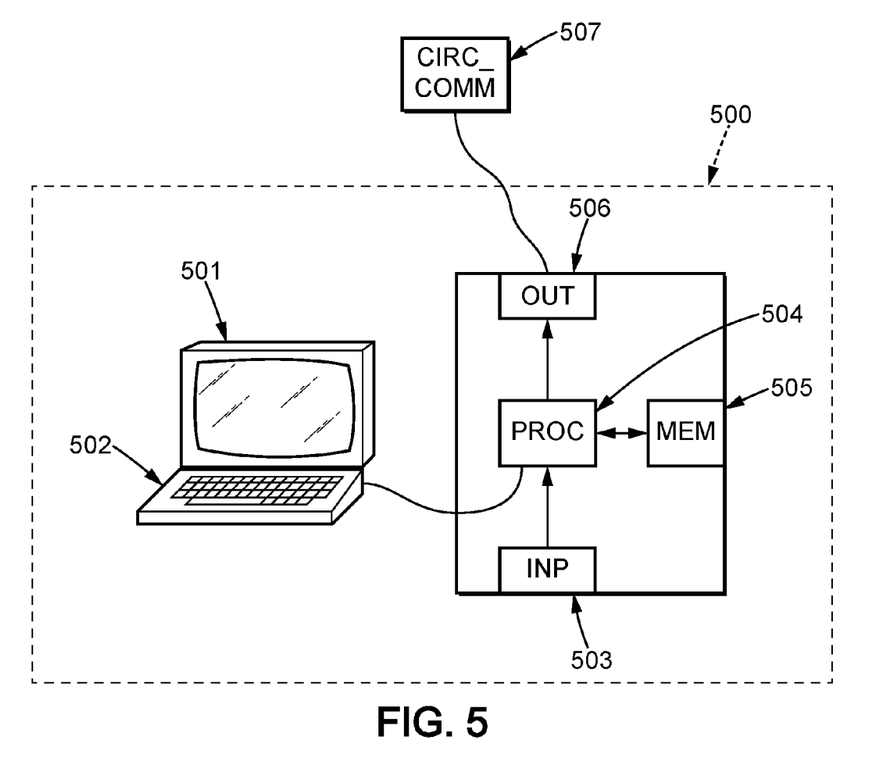
FIG. 5 is a possible embodiment for a device that enables the present invention.

Part of these flow charts (FIGS. 1 to 4) can represent steps of an example of a computer program which may be executed by the device of FIG. 5.

FIG. 5 is a possible embodiment for a device that enables the present invention.

In this embodiment, the device 500 comprise a computer, this computer comprising a memory 505 to store program instructions loadable into a circuit and adapted to cause circuit 504 to carry out the steps of the present invention when the program instructions are run by the circuit 504.

The memory 505 may also store data and useful information for carrying the steps of the present invention as described above.

The circuit 504 may be for instance:

a processor or a processing unit adapted to interpret instructions in a computer language, the processor or the processing unit may comprise, may be associated with or be attached to a memory comprising the instructions, or the association of a processor/processing unit and a memory, the processor or the processing unit adapted to interpret instructions in a computer language, the memory comprising said instructions, or an electronic card wherein the steps of the invention are described within silicon, or a programmable electronic chip such as a FPGA chip (for <<Field-Programmable Gate Array>>)).

This computer comprises an input interface 503 for the reception of data used for the above method according to the invention and an output interface 506 for providing the above mentioned data.

To ease the interaction with the computer, a screen 501 and a keyboard 502 may be provided and connected to the computer circuit 504.

Then, at least, the following thermodynamical properties of a fluid can be derived from determined values $x_n$, $Mw_n$, $\rho_n^0$ and $C(P,T)$ (see above):

$$Mw = \sum_{i=1}^{q} x_i \cdot Mw_i$$

$$\rho_L^0 = \frac{\sum_{i=p}^{q} x_i^L \cdot Mw_i}{\sum_{i=p}^{q} \frac{x_i^L \cdot Mw_i}{\rho_i^0}}$$

$$Bo = \frac{\sum_{i=1}^{q} \frac{x_i \cdot Mw_i}{\rho}}{\sum_{i=p}^{q} \frac{x_i \cdot Mw_i}{\rho_L^0}}$$

$$GOR = \frac{\sum_{i=1}^{p-1} \frac{x_i \cdot Mw_i}{\rho_G^0}}{\sum_{i=p}^{q} \frac{x_i \cdot Mw_i}{\rho_L^0}}$$

with p the rank to the first cut in the liquid phase and q the rank of the last cut in the liquid phase.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention.

In particular, it is apparent for the person skilled in the art that the invention may be enabled for any received cuts (e.g. if properties of cuts below k is known, it is possible to determine $\rho_{k+}^0(z)$ and not only $\rho_{6+}^0(z)$, $Mw_{k+}$ and not only $Mw_{6+}$, $Tc_{k+}$ and not only $Tc_{6+}$.

The invention claimed is:

1. A method for determining the fluid characteristics in a well, wherein said method comprises:

/a/ receiving a mass ratio by Downhole Fluid Analysis (DFA) measurements, each mass ratio being associated with a set of hydrocarbon cuts, and receiving a molecular ratio, said molecular ratio being associated with a set of hydrocarbon cuts;

/b/ converting received mass ratios into molecular ratios based on predetermined molecular weights, each predetermined molecular weights being associated with an element in the sets of hydrocarbon cuts;

/c/ normalizing converted molecular ratios with the received molecular ratio;

/d/ determining parameters $(\alpha, \beta)$ of a sequence defined by $$x_n = \alpha\left(1 - \frac{\beta}{n}\right)x_{n-1},$$

each normalized molecular ratio being associated with a member of the sequence or a sum of members of the sequence, at least a difference between said normalized molecular ratio and the associated member or the associated sum of members being minimized;

/e/ computing an estimated molecular weight ($Mw_{6+}$) function of $$\left(k + \frac{1}{1-\alpha}\right)\Delta M,$$

where k is an integer and $\Delta M$ is a predetermined value representing a molecular weight increment between two hydrocarbon cuts;

/f/ if a stabilization criteria is met, the steps /b/ to /f/ are iterated with the estimated molecular weight as one of the predetermined molecular weights in step /b/;

/g/ outputting the values of the parameters determined in step /d/ to predict the concentration of hydrocarbon cuts of a rank n, n being strictly higher than 6, and h/ quantify properties for the hydrocarbon cuts heavier than 6 to determine at least one in situ fluid characteristic chosen among API gravity, downhole density, gas oil ratio and formation volume factor.

2. A method according to claim 1, wherein the estimated molecular weight ($Mw_{6+}$) represents hydrocarbon cuts having more than k carbons.

3. A method according to claim 1, wherein the stabilization criteria of step /f/ comprises at least one following condition:

an absolute difference of a value of $\alpha$ between two iterations of steps /b/-/f/ is lower than a predetermined threshold;

an absolute difference of a value of the estimated molecular weight between two iterations of steps /b/-/f/ is lower than a predetermined threshold;

a number of iteration of steps /b/-/f/ exceeds a predetermined value.

4. A method according to claim 1, wherein $\Delta M$ is initially set to a value between 12 and 14.

5. A method according to claim 1, wherein $\Delta M$ is initially set a mean value for various fluids compositions examined in laboratory conditions.

6. A non-transitory computer readable storage medium, having stored thereon a computer program comprising program instructions, the computer program being loadable into a data-processing unit and adapted to cause the data-processing unit to carry out the steps of claim 1 when the computer program is run by the data-processing unit.

7. A method for determining a fluid characteristic for a plurality of elevation values $(z_1, z_2, z_3)$ in a well, wherein said method comprises:

/i/ determining a plurality of values Δ by executing for each of the elevation values ($z_1$, $z_2$, $z_3$) the steps of:

/a/ receiving mass ratios by Downhole Fluid Analysis (DFA) measurements, each mass ratio being associated with a set of hydrocarbon cuts, and receiving a molecular ratio, said molecular ratio being associated with a set of hydrocarbon cuts;

/b/ converting received mass ratios into molecular ratios based on predetermined molecular weights, each predetermined molecular weights being associated an element in the sets of hydrocarbon cuts;

/c/ normalizing converted molecular ratios with the received molecular ratio;

/d/ determining parameters (α,β) of a sequence defined by $x_n = \alpha(1-\beta n x_{n-1})$, each normalized molecular ratio being associated with a member of the sequence or a sum of members of the sequence, at least a difference between said normalized molecular ratio and the associated member or the associated sum of members being minimized;

/e/ computing an estimated molecular weight ($Mw_{6+}$) function of $$\left(k + \frac{1}{1-\alpha}\right)\Delta M,$$

where k being an integer and ΔM being a predetermined value representing a molecular weight increment between two hydrocarbon cuts;

/f/ if a stabilization criteria is met, the steps /b/ to /f/ are iterated with the estimated molecular weight as one of the predetermined molecular weights in step /b/;

/g/ outputting the values of the parameters determined in step /d/ to predict the concentration of a hydrocarbon cuts of rank n, n being strictly higher than 6, and /h/ quantify properties for the hydrocarbon cuts heavier than 6 to determine at least one in situ fluid characteristic chosen among API gravity, downhole density, gas oil ratio and formation volume factor;

/ii/ determining a mean molecular weight increment value by computing a plurality of values $$\frac{RT}{g(z_i - z_j)}\ln\left(\frac{\alpha(z_i)}{\alpha(z_j)}\right),$$

$z_i$) being an elevation value in the plurality of elevation values and $\alpha(z_i)$ being the determined value α in step /i/ for the elevation value $z_i$, $z_j$ being an elevation value in the plurality of elevation values different from $z_i$ and $\alpha(z_j)$ being the determined value α in step /i/ for the elevation value $z_j$;

/iii/ if a stabilization criteria is met, the steps /i/ to /iii/ are iterated with the mean molecular weight increment value as ΔM in step /d/;

/iv/ outputting the values of the parameters determined in step /i/ and the mean molecular weight increment value determined in step /ii/.

8. A method according to claim 7, wherein the stabilization criteria of step /iii/comprises at least one following condition:

an absolute difference of a value of the mean molecular weight increment value between two iterations of steps /i/-/iii/ is lower than a predetermined threshold;

a number of iteration of steps /i/-/iii/ exceeds a predetermined value.

* * * * *

UNITED STATES PATENT AND TRADEMARK OFFICE
CERTIFICATE OF CORRECTION

| | |
|---|---|
| PATENT NO. | : 10,378,348 B2 |
| APPLICATION NO. | : 15/026857 |
| DATED | : August 13, 2019 |
| INVENTOR(S) | : Caroli |

It is certified that error appears in the above-identified patent and that said Letters Patent is hereby corrected as shown below:

On the Title Page

<u>In the Abstract Column 2, Line 12:</u>
Add a ")" at the end of the formula $(k+11-\alpha\Delta M$ In the Claims <u>Column 15, Line 16 Claim 7:</u>
Add a ")" at the end of the formula $x_n = \alpha(1-\beta n x n-1$ Signed and Sealed this
Twenty-second Day of October, 2019

Andrei Iancu
*Director of the United States Patent and Trademark Office*